United States Patent
Imran

(10) Patent No.: US 8,423,131 B2
(45) Date of Patent: Apr. 16, 2013

(54) CORROSION RESISTANT ELECTRODES FOR IONTOPHORETIC TRANSDERMAL DELIVERY DEVICES AND METHODS OF USE

(75) Inventor: Mir Imran, Los Altos Hills, CA (US)

(73) Assignee: InCube Labs, LLC, San Jose, CA (US)

(*) Notice: Subject to any disclaimer, the term of this patent is extended or adjusted under 35 U.S.C. 154(b) by 208 days.

(21) Appl. No.: 12/824,146

(22) Filed: Jun. 25, 2010

(65) Prior Publication Data

US 2010/0331759 A1    Dec. 30, 2010

Related U.S. Application Data

(60) Provisional application No. 61/221,010, filed on Jun. 26, 2009.

(51) Int. Cl.
    *A61N 1/30*    (2006.01)
(52) U.S. Cl.
    USPC .............................. 604/20; 607/152
(58) Field of Classification Search ............. 607/152, 607/149; 604/20
    See application file for complete search history.

(56) References Cited

U.S. PATENT DOCUMENTS

| | | | |
|---|---|---|---|
| 3,491,187 A | 1/1970 | Ely | |
| 4,325,367 A | 4/1982 | Tapper | |
| 4,731,049 A | 3/1988 | Parsi | |
| 4,734,090 A | 3/1988 | Sibalis | |
| 4,886,489 A | 12/1989 | Jacobsen et al. | |
| 5,310,404 A | 5/1994 | Gyory et al. | |
| 5,328,453 A | 7/1994 | Sibalis | |
| 5,385,543 A | 1/1995 | Haak et al. | |
| 5,503,632 A | 4/1996 | Haak | |
| 5,605,536 A | 2/1997 | Sibalis | |
| 5,693,024 A | 12/1997 | Flower | |
| 5,797,867 A | 8/1998 | Guerrera et al. | |
| 5,928,185 A | 7/1999 | Muller et al. | |
| 5,983,130 A | 11/1999 | Phipps et al. | |
| 6,019,877 A * | 2/2000 | Dupelle et al. | 204/196.11 |
| 6,064,908 A | 5/2000 | Muller et al. | |
| 6,330,471 B1 | 12/2001 | Higo et al. | |
| 6,512,950 B2 | 1/2003 | Li et al. | |
| 6,553,255 B1 | 4/2003 | Miller et al. | |
| 6,689,275 B1 | 2/2004 | Gupta | |
| 6,731,965 B2 * | 5/2004 | Menon et al. | 600/396 |

(Continued)

FOREIGN PATENT DOCUMENTS

EP    0090425 A1    10/1983

OTHER PUBLICATIONS

International Preliminary Report on Patentability mailed Aug. 25, 2011 in PCT/US2010/023112.

(Continued)

*Primary Examiner* — Brian T Gedeon
(74) *Attorney, Agent, or Firm* — Mahamedi Paradice Kreisman LLP

(57) ABSTRACT

Embodiments of the invention provide electrode assemblies and associated methods for the iontophoretic transdermal delivery of therapeutic agents. Many embodiments provide a corrosion resistant electrode for the iontophoretic transdermal delivery of various therapeutic agents. Such embodiments allow for the iontophoretic transdermal delivery of therapeutic agents such as iron compounds for prolonged periods without any substantial corrosion of the electrode, impedance increases or discoloration or irritation of the skin. Embodiments of the invention are particularly useful for the long term treatment of various chronic medical conditions such as iron deficient anemia.

27 Claims, 9 Drawing Sheets

U.S. PATENT DOCUMENTS

| | | |
|---|---|---|
| 6,779,468 B1 | 8/2004 | Gupta |
| 7,137,975 B2 | 11/2006 | Miller et al. |
| 7,340,297 B2 | 3/2008 | Tamarkin et al. |
| 7,375,139 B2 | 5/2008 | Aldred |
| 7,437,189 B2 | 10/2008 | Matsumura et al. |
| 7,496,401 B2 | 2/2009 | Bernabei |
| 7,522,954 B2 | 4/2009 | Tedoldi |
| 7,548,778 B2 | 6/2009 | Roy |
| 7,558,625 B2 | 7/2009 | Levin et al. |
| 7,590,444 B2 | 9/2009 | Tanioka |
| 7,593,770 B2 | 9/2009 | Lerner |
| 7,611,481 B2 | 11/2009 | Cleary et al. |
| 7,816,404 B2 | 10/2010 | McCall, Jr. |
| 2003/0060798 A1 | 3/2003 | Fischer et al. |
| 2003/0199808 A1 | 10/2003 | Henley et al. |
| 2004/0138646 A1 | 7/2004 | Walla |
| 2005/0020487 A1 | 1/2005 | Klaus et al. |
| 2005/0085751 A1 | 4/2005 | Daskal et al. |
| 2005/0165393 A1 | 7/2005 | Eppstein |
| 2005/0209565 A1 | 9/2005 | Yuzhakov |
| 2005/0213286 A1 | 9/2005 | Michel et al. |
| 2005/0238704 A1 | 10/2005 | Zumbrunn et al. |
| 2005/0273046 A1 | 12/2005 | Kwiatkowski et al. |
| 2006/0025715 A1 | 2/2006 | Henley et al. |
| 2006/0216339 A1 | 9/2006 | Ambron et al. |
| 2006/0229549 A1 | 10/2006 | Hause et al. |
| 2006/0258973 A1 | 11/2006 | Volt |
| 2007/0065521 A1 | 3/2007 | Venkataraman et al. |
| 2007/0066934 A1 | 3/2007 | Etheredge et al. |
| 2007/0083185 A1 | 4/2007 | Carter |
| 2007/0083186 A1 | 4/2007 | Carter et al. |
| 2007/0224253 A1 | 9/2007 | Franklin |
| 2008/0027369 A1 | 1/2008 | Carter et al. |
| 2008/0058699 A1 | 3/2008 | Hause et al. |
| 2008/0058700 A1 | 3/2008 | Hause et al. |
| 2008/0081051 A1 | 4/2008 | Sabin et al. |
| 2008/0114282 A1 | 5/2008 | Carter |
| 2008/0154178 A1 | 6/2008 | Carter et al. |
| 2008/0287497 A1 | 11/2008 | Anderson et al. |
| 2009/0036821 A1 | 2/2009 | Lai |
| 2009/0062720 A1 | 3/2009 | Anderson et al. |
| 2009/0124572 A1 | 5/2009 | Nelson |
| 2009/0163597 A1 | 6/2009 | Goto et al. |
| 2009/0171313 A1 | 7/2009 | Yamamoto et al. |
| 2009/0221985 A1 | 9/2009 | Bukshpan et al. |
| 2009/0254018 A1 | 10/2009 | Nakayama |
| 2009/0259176 A1 | 10/2009 | Yairi |
| 2009/0281475 A1 | 11/2009 | Nisato et al. |
| 2009/0299264 A1 | 12/2009 | Matsumura et al. |
| 2009/0299267 A1 | 12/2009 | Durand |
| 2010/0204637 A1 | 8/2010 | Imran |
| 2010/0331811 A1 | 12/2010 | Imran |
| 2011/0082411 A1 | 4/2011 | Imran |

OTHER PUBLICATIONS

International Preliminary Report on Patentability mailed Aug. 25, 2011 in PCT/US2010/023744.
International Search Report, Written Opinion and Notice of Transmittal of Same mailed Feb. 25, 2011 in PCT/US2010/040109.
International Search Report, Written Opinion and Notice of Transmittal of Same mailed Jun. 24, 2011 in PCT/US2010/051541.
International Search Report, Written Opinion and Notice of Transmittal of Same mailed Sep. 27, 2010 in PCT/US2010/023744.
International Search Report, Written Opinion and Notice of Transmittal of Same mailed Sep. 27, 2010 in PCT/US2010/023112.
Murhty et al., "Irontophoresis™: Transdermal Delivery of Iron by Iontophoresis," J. Pharm. Sci., 98(8): 2670-2676 (Aug. 2009).
Non-Final Office Action mailed Apr. 8, 2011 in U.S. Appl. No. 12/537,243.
Final Office Action mailed Oct. 28, 2011 in U.S. Appl. No. 12/537,243.
International Preliminary Report on Patentability mailed Jan. 12, 2012 in PCT/US2010/040109.
Notice of Allowance mailed Jan. 19, 2012 in U.S. Appl. No. 12/537,243.
Non-Final Office Action issued in U.S. Appl. No. 12/658,637, dated Mar. 23, 2012.
Notice of Allowance issued in U.S. Appl. No. 12/658,637, dated Jul. 9, 2012.
International Preliminary Report on Patentability as issued in related International Application PCT/US2010/051541, dated Apr. 19, 2012.
Non-final Office Action mailed in U.S. Appl. No. 12/824,147, dated Jun. 1, 2012.

* cited by examiner

CORROSION RESISTANT ELECTRODES FOR IONTOPHORETIC TRANSDERMAL DELIVERY DEVICES AND METHODS OF USE

RELATIONSHIP TO OTHER APPLICATIONS

This application claims the benefit of priority to Provisional U.S. Patent Application No. 61/221,010, entitled "Corrosion Resistant Electrodes for Iontophoretic Transdermal Delivery Devices", filed Jun. 26, 2009; the aforementioned priority application being hereby incorporated by reference for all purposes.

This application is also related to concurrently filed application entitled "Corrosion Resistant Electrodes for Iontophoretic Transdermal Delivery Devices and Methods of Use.", which is being hereby incorporated by reference in its entirety for all purposes.

FIELD OF THE INVENTION

Embodiments described herein relate to electrode assemblies for iontophoretic transdermal delivery devices used for the delivery of various therapeutic agents. More specifically, embodiments described herein relate to conductive materials for electrode assemblies for iontophoretic transdermal delivery devices.

BACKGROUND

Iontophoresis is a non-invasive method of propelling high concentrations of a charged substance, known herein as the active agent, transdermally by repulsive electromotive force using a small electrical charge. The active agent can include a drug or other therapeutic agent. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation into the skin.

Over time, metal electrodes used in iontophoretic transdermal patches may become corroded due to electrochemical corrosion of the metal during current flow through the electrode. Corrosion can increase the electrical impedance of the patch, decreasing the current delivered from that patch to the skin with a resulting decrease in the delivery rate of therapeutic agents from the patch. There is a need for electrochemically corrosion resistant electrode materials used in iontophoretic transdermal patches.

BRIEF DESCRIPTION OF THE DRAWINGS

FIG. 5a shows an embodiment having a substantially disc shape. FIG. 5b shows an embodiment having a substantially oval shape.

FIG. 6a shows an embodiment where the diameter of the electrode is smaller than the diameter of the tissue contacting layer. FIG. 6b shows an embodiment where the electrode and the porous layer have substantially the same diameter.

FIG. 7a shows an embodiment having a substantially squared edge; FIG. 7b shows an embodiment having a substantially rounded edge; FIG. 7c shows an embodiment having at least a partially tapered edge; and FIG. 7d shows an embodiment of the electrode having a concave contour.

DETAILED DESCRIPTION OF THE INVENTION

Figure 1:
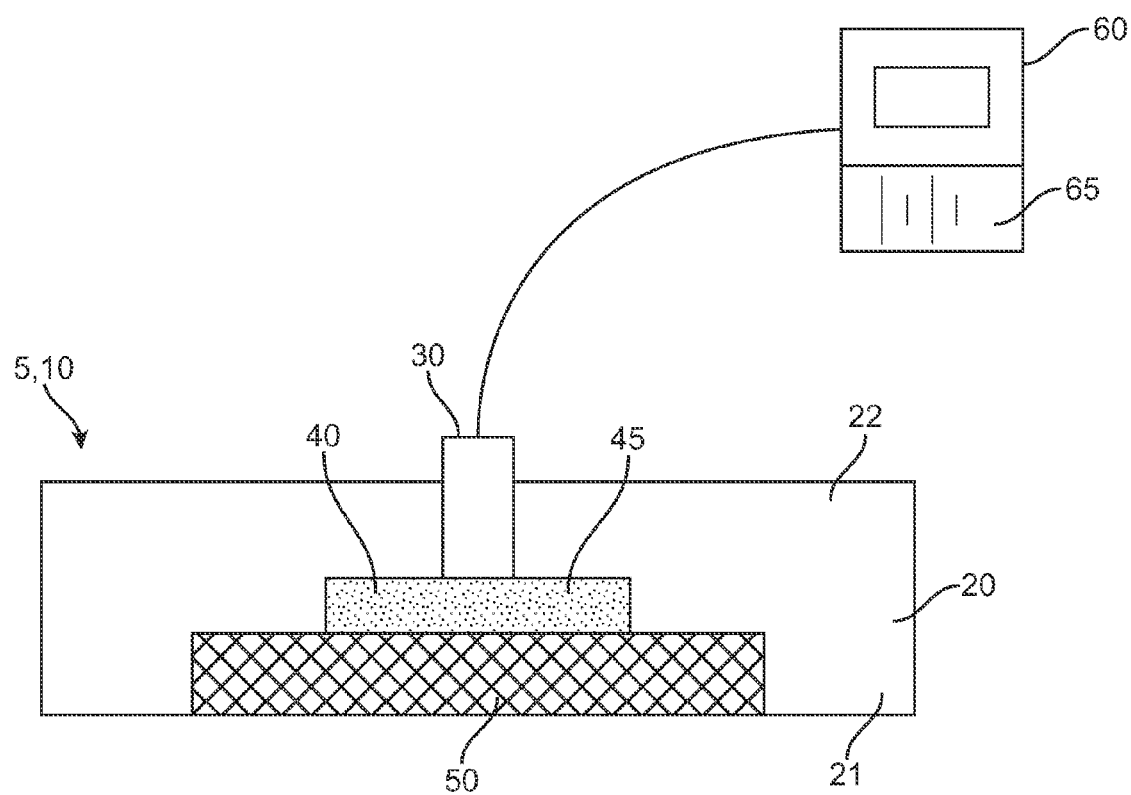
FIG. 1 is a lateral view showing an embodiment of a corrosion resistant electrode assembly for an iontophoretic transdermal delivery of a therapeutic agent.

Embodiments described herein provide electrode assemblies for the iontophoretic transdermal delivery of therapeutic agents. Many embodiments provide a corrosion resistant electrode for the transdermal delivery of therapeutic agents. Such embodiments can be utilized for the delivery of a number of therapeutic agents including the delivery of iron containing compounds for the treatment of iron deficiency anemia and other iron deficiency diseases and conditions.

One embodiment provides a corrosion resistant electrode assembly for the iontophoretic transdermal delivery of a therapeutic agent, the electrode assembly comprising a conformable layer conformable to a contour of a skin surface and having a tissue contacting side and non-tissue contacting side; an electrical connector positioned on the non-tissue contacting side of the conformable layer, an electrode operatively coupled to the connector; and a tissue contacting porous layer positioned on the tissue contacting side of the conformable layer and operatively coupled to the electrode. The electrical connector is configured to be operatively coupled to an electrical power source such as an alkaline or lithium battery or other portable power source. The electrode is at least partially disposed in the porous layer.

In some embodiments, the electrode comprises a graphite or other electrochemically un-reactive material such that the electrode does not substantially corrode when current flows through the electrode from the power source during periods of iontophoretic transdermal delivery of the therapeutic agent.

Additionally, some embodiments provide that the electrode is structured to have sufficient corrosion resistance such that the impedance through the electrode does not substantially increase during periods of current flow through the electrode, for example, for periods of 12 to 96 hours or longer. Additionally, the electrode comprises a material which is sufficiently corrosion resistant and chemically inert such that it will not cause any appreciable discoloration or irritation of the skin from any corrosion that may occur.

In preferred embodiments, the electrode comprises a flexible compressed graphite material. Other graphites or organic compositions such as pyrolytic graphite are also considered. In alternative embodiments, the electrode can comprise a carbon impregnated polymer such as rubber or even polymer fibers such as cotton, polyesters, polysulphone or other polymeric fibers known in the art.

Typically, the electrode will have a thin disc shape with a preferred thickness of about 0.5 mm to about 2 mm. However, other shapes and thicknesses are also contemplated such as an oval shape. For disc and other shaped embodiments, the edges of the electrode can be square, rounded with a selected radius or even tapered partially or fully to minimize any electrical edge effects (e.g., current concentrations/increased current density at the electrode edges and resulting ohmic or other heating). The entire disc can also have a concave/dogbone contour to minimize edge effects by having the electrode have a larger thickness on the edges. In various embodiments, the electrode can be sized such that it has substantially the same surface area (e.g., diameter for disc shaped embodiments) as the underlying tissue contacting porous layer or it may have a smaller surface area, for example, 50% or 25% of the surface area of the porous layer. No matter what the size, the electrode can be centered above the tissue contacting porous layer, such that it is concentric with respect to the porous layer, though eccentric configurations are also contemplated.

In some embodiments, the electrode can also be sufficiently flexible so that it can bend and flex with the entire electrode assembly in order to conform to the contour of the skin surface. However, stiffer embodiments are also contemplated. Also, typically the electrode will be placed in direct contact with the tissue contacting porous layer and positioned directly above it relative to the non-tissue contacting side of the conformable layer. However, the electrode may also be operatively electrically coupled to the porous layer through an intermediary conductive material.

The tissue contacting porous layer is operatively coupled to the electrode such that the current from the electrode flows into the porous layer. In many embodiments, the porous layer will be in direct contact with the electrode, though use of an intermediary conductor is also contemplated to electrically couple the two structures. The porous layer can comprise compressed cotton or other fiber such as a polyester fiber or polysulphone and may be woven. The porous layer may have a sufficiently tight weave or other configuration such that it can capture any pieces of electrode material that break off from the electrode due to small amounts of corrosion during periods of current flow through the electrode.

In various embodiments, the electrode assembly can also include a reservoir for a solution containing the therapeutic agent. Typically, the electrode will be placed in direct contact with the reservoir, however, it may also be offset from the reservoir and operatively electrically coupled to it through an intermediary conductor. In embodiments having a reservoir, the electrode material comprises graphite or other material sufficiently resistant to electrochemical corrosion by an aqueous based therapeutic agent solution.

Still further, many embodiments include provide corrosion resistant electrodes and corrosion resistant electrode assemblies for use with iontophoretic transdermal delivery devices, such as various skin conformable patches for the iontophoretic transdermal delivery of various therapeutic agents (also described herein as the active agent). Such agents can include, for example, insulin, antibiotics, analgesics, chemotherapeutics and iron containing compounds for the treatment of anemia. Suitable iron compounds can comprise ionic iron in the form of ferrous ($Fe^{2+}$) or ferric ($Fe^{3+}$) iron. The ionic iron can comprise an iron salt, a ferrous salt, a ferric salt, ferric pyrophosphate, ferrous chloride or a combination thereof. Still other iron containing compounds known in the anemia treatment arts are also contemplated.

In specific embodiments, the active agent can comprise a sufficient amount of elemental iron for the treatment of iron deficiency anemia. The amount of elemental iron can be sufficient to provide between 1 to 100 mg of elemental iron to the patient a day for a period of days or even weeks. Further description on suitable iron compounds for the treatment of iron deficient anemia and like conditions may be found in U.S. patent application Ser. No. 12/459,862, filed Jul. 7, 2009 and entitled "Method For Transdermal Iontophoretic Delivery Of Chelated Agents", which is fully incorporated by reference herein for all purposes.

Figure 2:
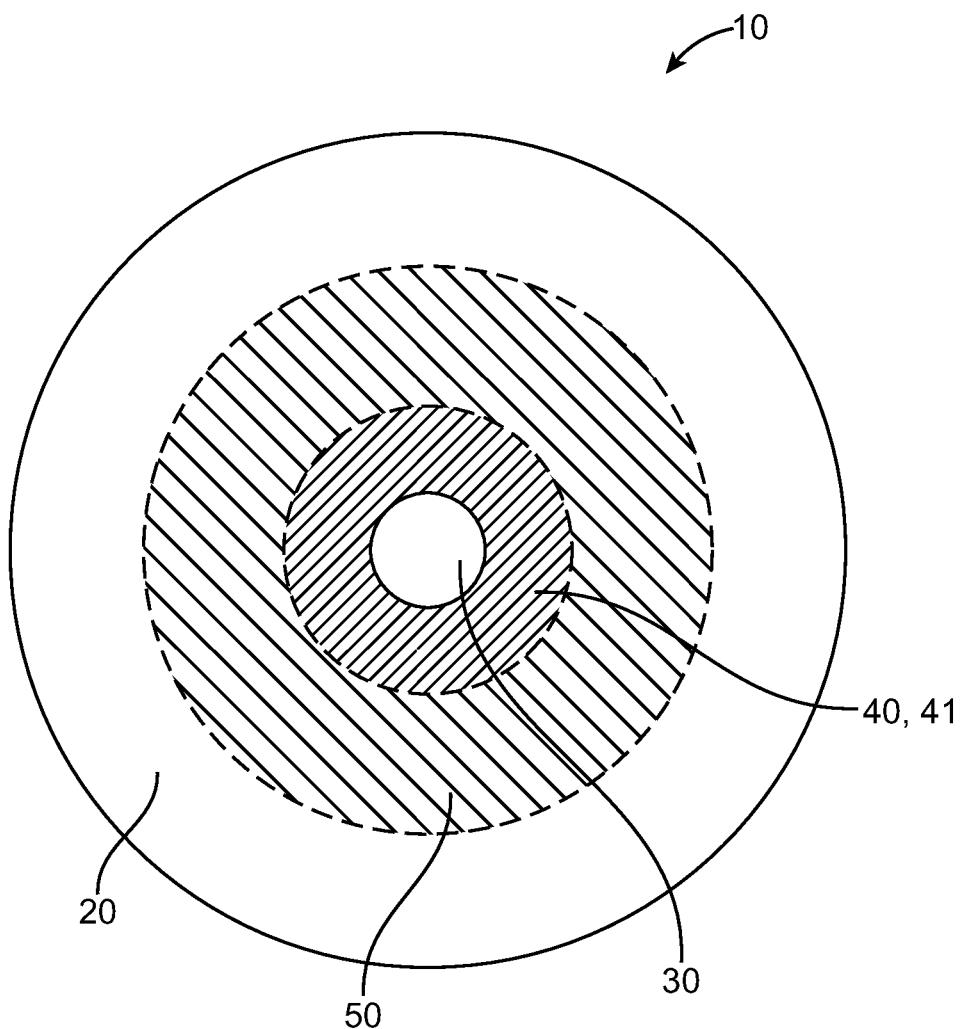
FIG. 2 is a top down view of the embodiment of FIG. 1.

Referring now to FIGS. 1-2, an embodiment of a corrosion resistant electrode assembly 10 for use with a iontophoretic transdermal delivery device 5 such as a patch device 5, comprises a conformable layer 20, an electrical connector 30, an electrode 40 and a porous tissue contacting layer 50. Conformable layer 20 is conformable to the contour of a skin surface and has a skin contacting side 21 and non-skin contacting side 22. The conformable layer 20 can comprise various elastomeric polymers known in the art such as polyurethane or silicone and has sufficient flexibility to not only conform to a contour of the skin surface but also to bend and flex with movement of the skin.

Electrical connector 30, hereafter connector 30, is typically positioned on the non-tissue contacting side 22 of conformable layer 20 and comprises any number of standard electrical connectors such as various nipple connectors known in the medical instrument and electronics arts. The connector 30 is also directly or otherwise "electrically operatively" (hereinafter "operatively") coupled to electrode 40. It is also configured to be coupled to an electrical power source 60 which may comprise one or more portable batteries 65 such as alkaline, lithium, lithium ion or other battery chemistry known in the art.

Electrode 40 includes an electrochemically corrosion resistant material (hereinafter "corrosion resistance") such that the electrode 40 does not undergo appreciable amounts of electrochemical corrosion (e.g., by oxidation or other related reactions) resulting from current flow through the electrode during iontophoretic transdermal delivery of the therapeutic agent or from any other current flow or electrical potential applied to the electrode.

Figure 3:
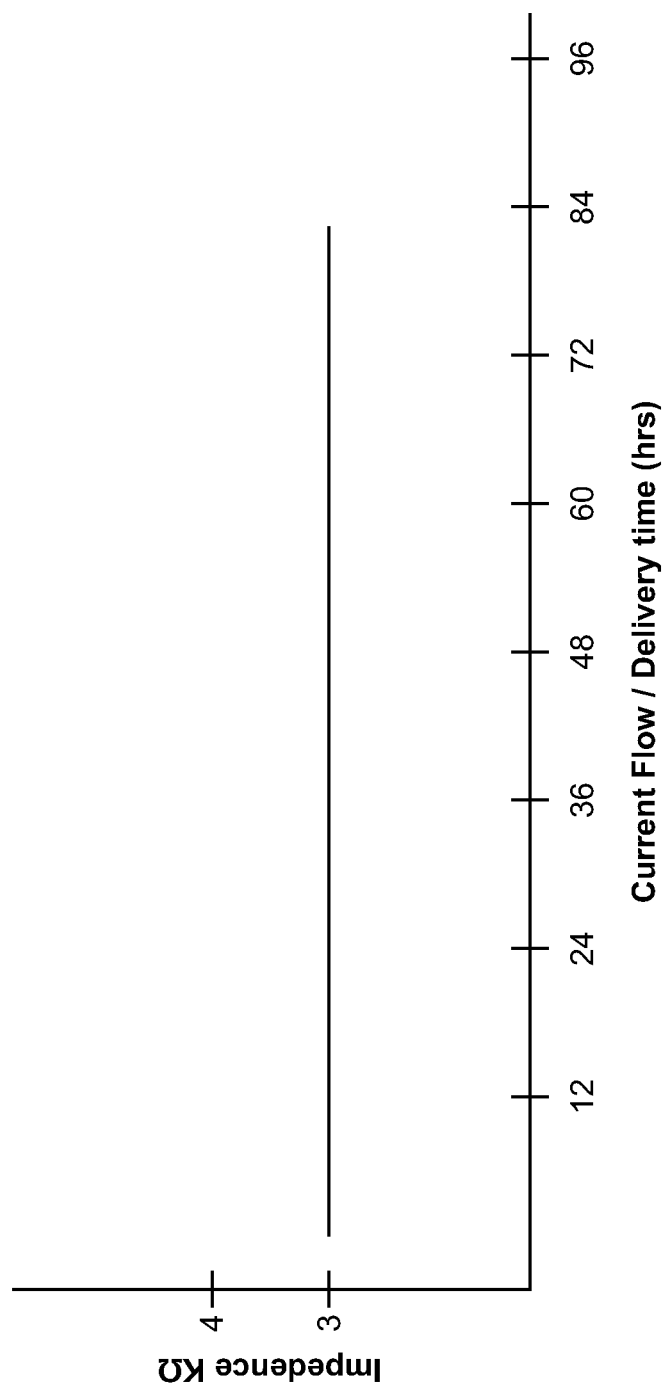
FIG. 3 is a prophetic plot showing the impedance for an embodiment of a corrosion resistant electrode during a period of current flow through the electrode and transdermal/iontophoretic delivery of a therapeutic agent.

The corrosion resistance of electrode 40 is also configured such that the conductive surface area 40SAC of the electrode is substantially preserved during periods of iontophoretic transdermal drug delivery. The preservation of surface area 40SAC in turn prevents any substantial increase in impedance of electrode 40. In specific embodiments, electrode 40 is configured to resist corrosion and maintain a substantially constant impedance or otherwise resist any appreciable impedance increases for currents in the range of 0.1 ma to 10 ma and voltage from 1 v to 100 v for periods of current flow of 12, 24, 48, 72 or 96 hours or longer as is shown in FIG. 3.

Among other benefits, embodiments of a corrosion resistant electrode 40 provide several benefits for iontophoretic transdermal delivery of various therapeutic agents such as iron containing compounds, insulin, etc. These can include allowing the maintenance of a substantially constant voltage applied to an iontophoretic transdermal patch device during a period of iontophoretic transdermal delivery and/or keeping the voltage below a desired threshold. The applied voltage is used in iontophoretic transdermal delivery to provide the electromotive driving force for propelling charged therapeutic agents, such as ionic iron compounds, into the skin. If the impedance of the electrode increases as a result of corrosion, larger voltages may be required. Maintaining a substantially constant voltage during a period of iontophoretic delivery, or keeping it below a selected threshold, serves to increase battery life, (for embodiments of battery-powered iontophoretic patch devices) and reduces the likelihood of pain perception of the user by keeping the voltage below a pain threshold.

In particular embodiments, the voltage can be kept below a threshold of about 100 volts and still more preferably below about 40 volts. Additionally, having a corrosion resistant electrode can also allow the current density associated with electrode 40 and/or electrode assembly 10 to be kept below a threshold (for example, the threshold for causing pain to the patient). This is due to the fact that the conductive surface area 40SAC of the electrode 40 remains substantially intact during the course of current delivery. In particular embodiments, the current density threshold associated with electrode 40 and/or electrode assembly 10 can be kept below about 1.0 ma/cm$^2$, more preferably below about 0.8 ma/cm$^2$, still more preferably below about 0.5 ma/cm$^2$ and still more preferably below about 0.2 ma/cm$^2$. Still lower values for the current density are contemplated.

As an addition or alternative, electrode 40 comprises a material which is sufficiently corrosion resistant and chemically inert such that it will not cause any appreciable discoloration or irritation/inflammation of the skin or other foreign body response from any amount of corrosion that may occur (e.g., resulting in contact or penetration of the electrode material into the skin). In various embodiments, these results can be achieved by the selection of a carbon-based electrode material such as graphite, which is both corrosion resistant and relatively chemically inert to body tissue.

In many embodiments, electrode 40 comprises a conductive graphite material. Graphite is a layered carbon material in which the layers comprise hexagonal lattices of carbon atoms. Graphite can conduct electricity due to extensive electron dislocations within each layer. In preferred embodiments, the electrode comprises a flexible compressed graphite material such as a flexible graphite sheet which can be fabricated using a calendaring or other compression process known in the art. In such embodiments, the graphite material can have sufficient flexibility to allow the electrode 40 to flex along with the rest of electrode assembly 10 so as to conform to the contour of the skin at a selected application site. An example of a suitable graphite includes grade INTRS-PGS394 having a thickness of about 0.06" available from the GraphiteStore.com (Buffalo Grove, Ill.).

Embodiments include use of other graphites such as pyrolytic graphite. Pyrolytic graphite is a unique form of graphite manufactured by decomposition of a hydrocarbon gas at very high temperature in a vacuum furnace. The result is an ultra-pure product which is near theoretical density and extremely anisotropic. Specific embodiments of pyrolytic graphite electrode 40 can be configured to allow for the electrical conduction through the electrode, but provide for thermal insulation in one or more directions.

Figure 4:
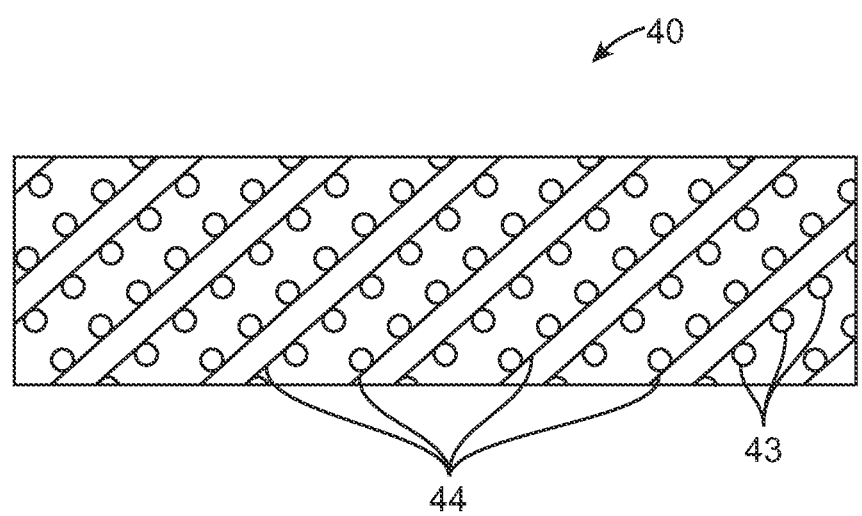
FIG. 4 is a lateral view showing an alternative embodiment of a corrosion resistant electrode comprising carbon impregnated fibers.

In alternative embodiments, electrode 40 can comprise a graphite/carbon impregnated including polymer fibers such as cotton, polyesters, polysulphone other polymeric fibers known in the art. An example of a carbon/graphite impregnated fiber is shown in the embodiment of FIG. 4. In this embodiment, particles 43 of graphite powder are bound to fibers 44. In other alternative embodiments, a corrosion resistant electrode 40 can comprise a carbon impregnated rubber or other carbon impregnated solid polymer, which can comprise various resilient polymers known in the art, allowing the electrode to bend and flex to conform to the contour of the skin surface. In use, such embodiments allow current to be delivered from an electrode assembly (including at least a portion of the electrode) in a bent position while preventing or minimizing any impedance rise in the electrode assembly due to corrosion of the electrode.

Still other alternative embodiments of a corrosion resistant electrode 40 can comprise carbon fibers (either turbostratic or graphitic carbon, or with a hybrid structure having both graphitic and turbostratic parts). In such embodiments, a disc or other shaped electrode 40, can be cut from a carbon fiber rod. In still other alternative embodiments, a corrosion resistant electrode can comprise carbon black material, for example, compressed carbon black powder, or polymer, such as polymer fibers impregnated with carbon black.

Figure 5A:
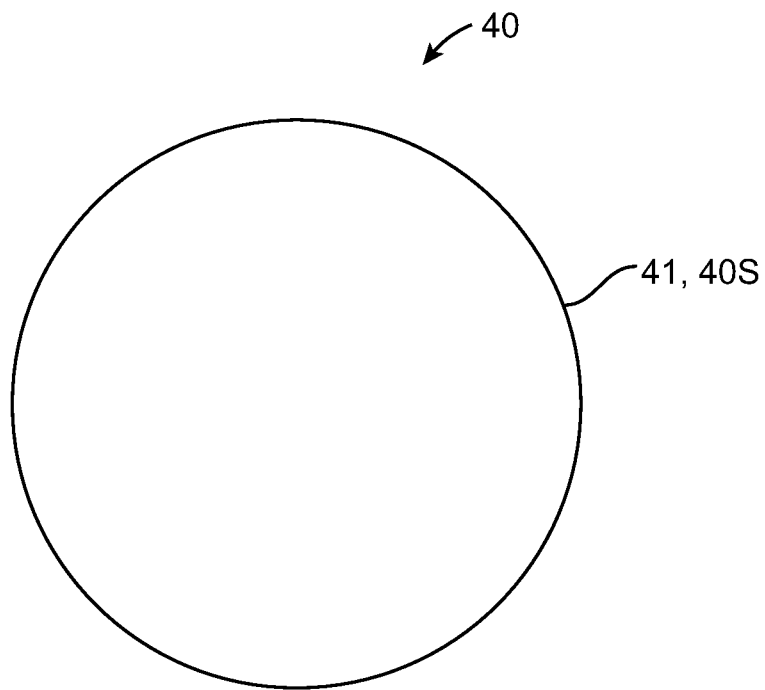
FIGS. 5a and 5b are top views showing different embodiments for the shape of the electrode.
Figure 5B:
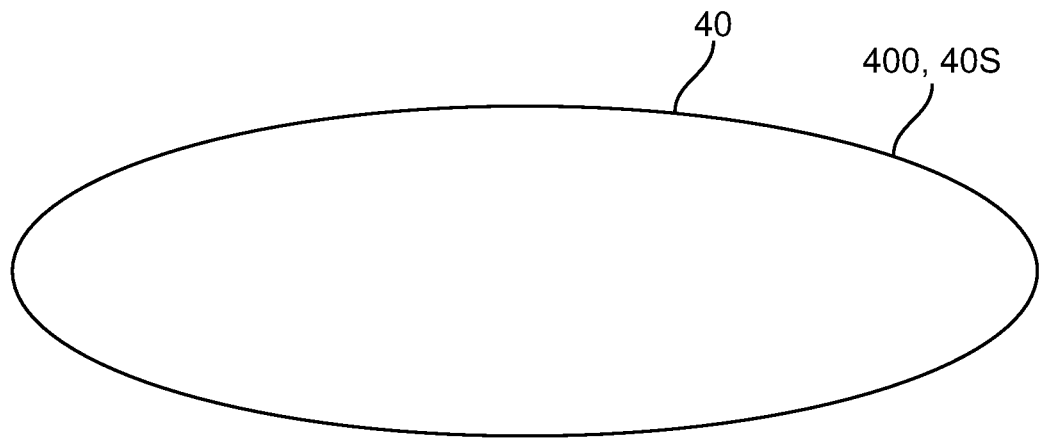

Typically, the electrode 40 will have a thin disc shape 41 as is shown in the embodiments of FIGS. 2 and 5a. However, other shapes 40s are also contemplated, such as an oval shape 40o as is shown in the embodiment of FIG. 5b which can be use in an oval shaped patch device 5. The thickness 40t of the electrode 40 is selected to allow for both flexibility (e.g., to conform to the contour of the skin surface) and corrosion resistance of the electrode. In preferred embodiments, electrode 40 has a thickness 40t in the range of about 0.5 to about 2 mm. Other ranges of thickness are also contemplated, for example, about 2 mm to about 4 mm. Increased thickness's can be selected where more stiffness in electrode 40 is desired.

Typically, electrode 40 will be placed in direct contact with the tissue contacting porous layer 50 and positioned directly above it relative to the non-tissue contacting side 22 of the conformable layer 20. In alternative embodiments, it may also be operatively electrically coupled to the porous layer through an intermediary conductive material (not shown). In still other alternative embodiments, portions of electrode 40 can be wrapped around porous layer 50 so that portions of the electrode are on the top and the sides of the porous layer 50.

According to some embodiments, the electrode 40 can be positioned in various locations in or on conformable layer 20. In preferred embodiments, electrode 40 is fully disposed within layer 20, so that it is electrically insulated, but also may have all or a portion positioned on the tissue 21 or non-tissue contacting sides 22 of layer 20. In these embodiments, the electrode 40 has an insulated coating (not shown) for those portions which are exposed. In some embodiments, all or a portion of electrode 40 can be placed in close proximity to the tissue contacting side 21, (e.g., within 0.01" or less).

Figure 6A:
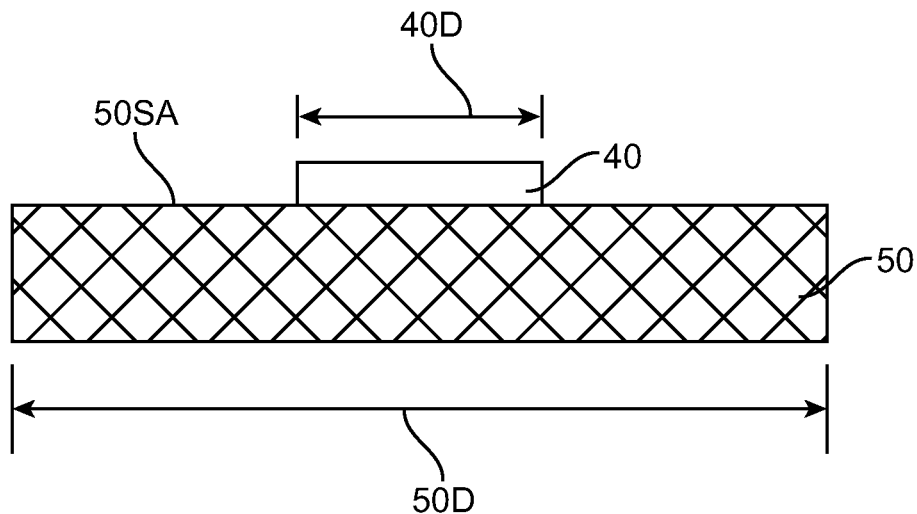
FIGS. 6a and 6b are lateral views showing different embodiments for the diameter of the electrode relative to the diameter of the porous tissue contacting layer.
Figure 6B:
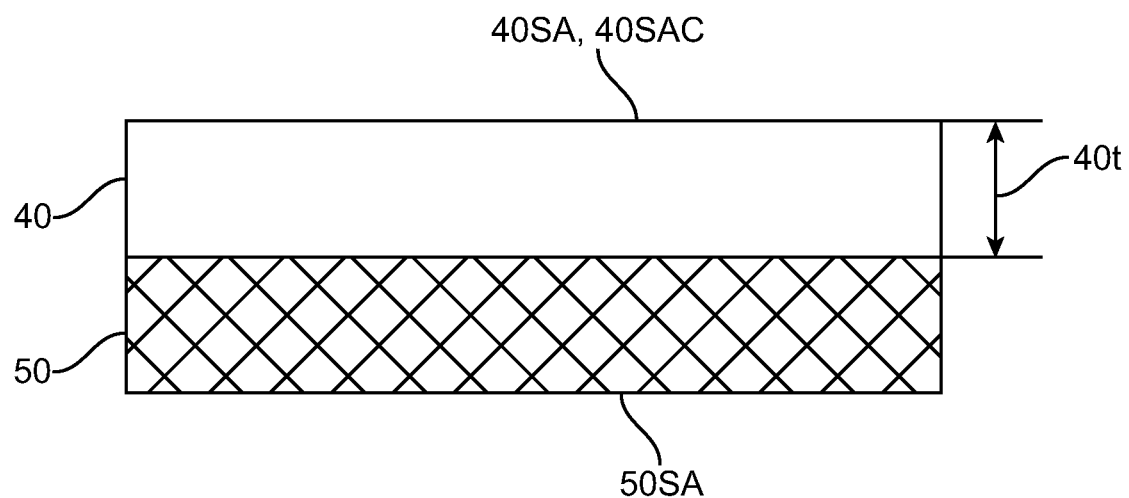

Electrode 40 can have a variety of sizes depending one or more on the amount of conductive surface area 40SAC desired, as well as the size of the underlying porous layer 50 and the various electrical parameters (e.g., current voltage, etc.) used for the iontophoretic transdermal delivery of therapeutic agent 85. In various embodiments, electrode 40 can be sized such that it has substantially the same surface area 40SA (and diameter 40D for disc shaped embodiments of the electrode) as the surface area 50SA (and diameter 50D for disc shape embodiments of the porous layer) for the underlying tissue contacting porous layer 50, as is shown in the embodiment of FIG. 6b. Alternatively, it may have a smaller surface area as is shown in the embodiment of FIG. 6a, for example, 50% to 25% of the surface area 50SA of porous layer 50. No matter what the size, the electrode is centered above the tissue contacting porous layer 50, such that it is concentric with respect to the porous layer, though eccentric configurations are also contemplated.

Figure 7A:
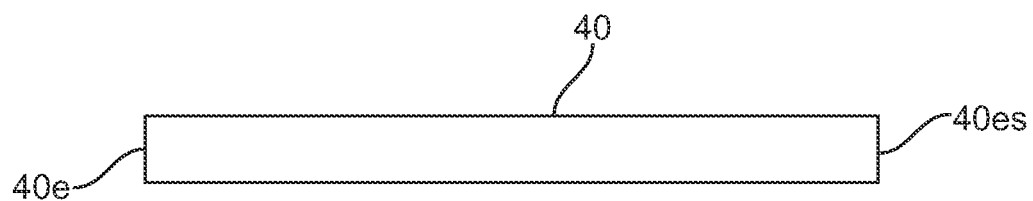
FIGS. 7a-7d are lateral views showing different embodiments for the contour of the edges of the electrode.
Figure 7B:
Figure 7C:
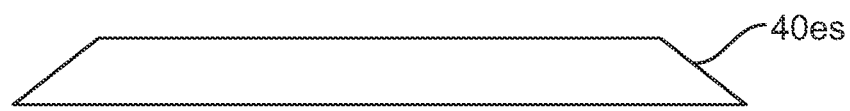
Figure 7D:
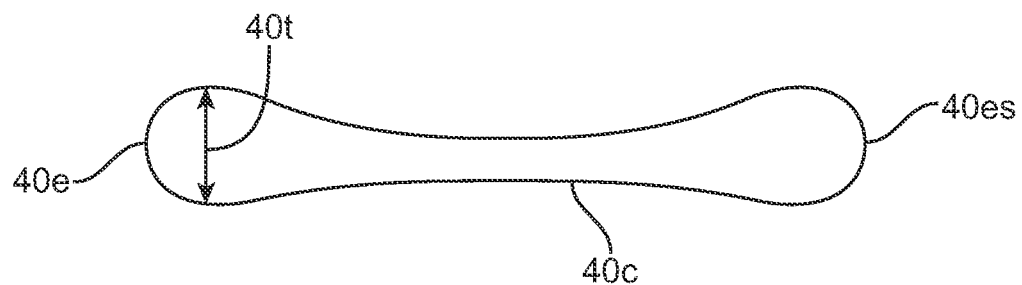

Referring now to FIGS. 7a-7d, in various embodiments, the edges 40e of electrode 40 can also have a selectable shape 40es depending upon one or more of the size of the electrode and various electrical parameters (e.g., current, voltage, etc.) used for a particular iontophoretic transdermal patch 5. In particular embodiments, the shape 40es of edge 40e can be square (shown in the embodiment of FIG. 7a) or rounded with a selected radius (shown in the embodiment of FIG. 7b) to minimize any edge effects or even tapered (shown in the embodiment of FIG. 7c). For disc shaped embodiments of electrode 40, the entire electrode can have a concave/dogbone contour 40c to minimize edge effects by having the electrode have a larger thickness 40t on the edges 40e (as is shown in the embodiment of FIG. 7d).

Referring back to FIGS. 1-6, tissue contacting porous layer 50 is operatively coupled to the electrode 40 such that the current from the electrode flows into the porous layer. In many embodiments the porous layer 50 is in direct contact with electrode 40 as is shown in the embodiment of FIG. 1. However, in other embodiments, such as in the embodiment of FIG. 8, the use of an intermediary conductor, (in this case, a conductive therapeutic agent solution) is also contemplated to electrically couple the two structures. In various embodiments, porous layer 50 can comprise various fibers such as a polyester (e.g., PET) or polysulphone fiber and may be compressed and/or woven. Various polymeric foams may also be used. In preferred embodiments, the porous layer comprises compressed cotton. In one embodiment, the porous layer 50 has a sufficiently tight weave or other related property (e.g., porosity) such that it can capture any piece of electrode material that breaks off from electrode 40 due to small amounts of corrosion during periods of current flow through the electrode. In particular embodiments, the porous materials may also include various chemical functional groups or coatings selected to bind the graphite or other electrode material to provide an additional means for preventing the corrosive breakdown of electrode 40 and/or capturing pieces of corroded electrode 40 before they break off.

Figure 8:
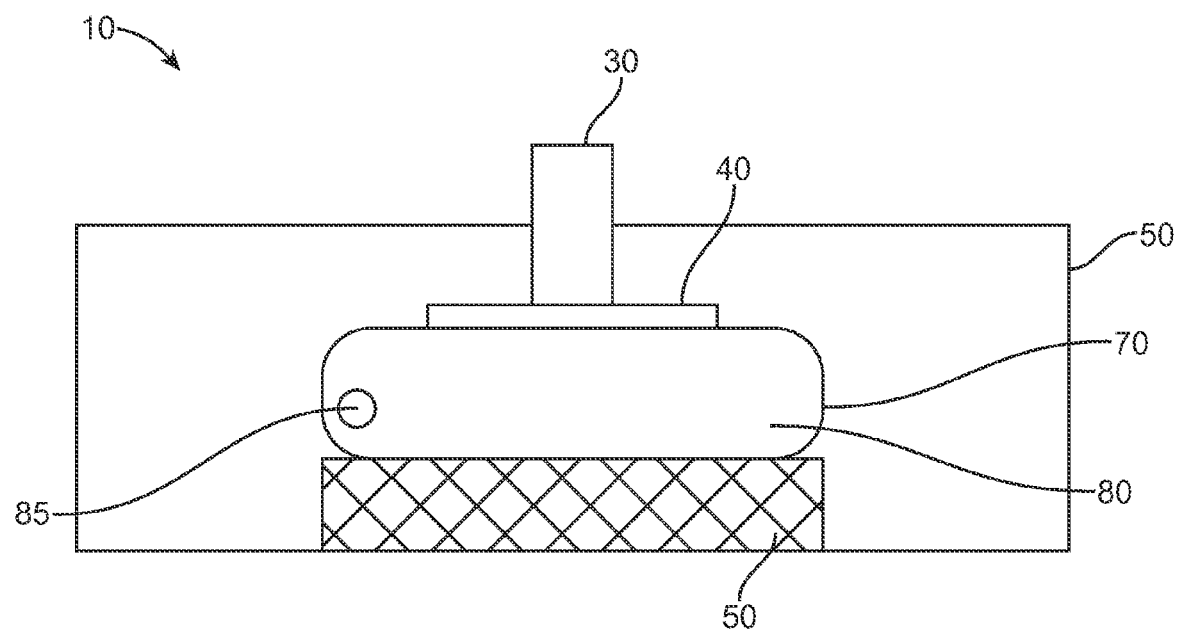
FIG. 8 is a lateral view showing an embodiment of a corrosion resistant electrode assembly including a reservoir for therapeutic agent where the electrode is positioned adjacent the reservoir.
Figure 9:
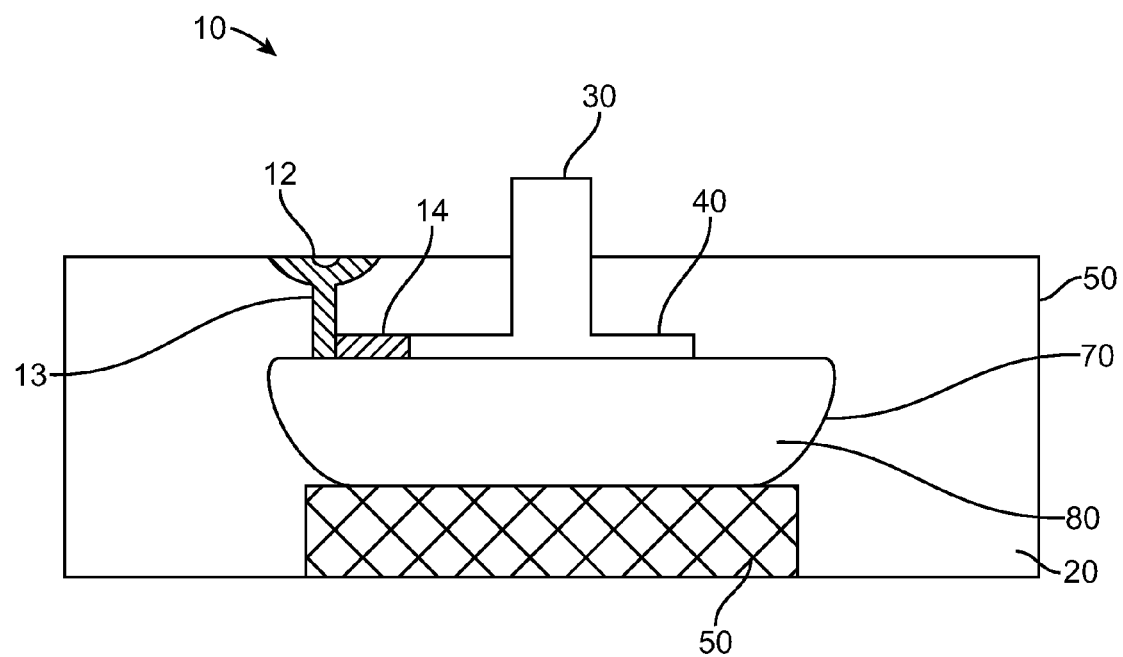
FIG. 9 is a lateral view showing an embodiment of a corrosion resistant electrode assembly including a reservoir and a self sealing port for filling the reservoir with a therapeutic agent solution.

Referring now to FIGS. 8-9, in various embodiments, electrode assembly 10 can also include a reservoir 70 for a solution 80 containing a therapeutic agent 85 as is shown in the embodiments of FIGS. 8 and 9. Typically, in such embodiments, electrode 40 will be placed in direct contact with reservoir 70; however, it may also be offset from reservoir 70 a selected distance and operatively, electrically coupled to it through an intermediary conductor (not shown). In embodiments having a reservoir 70, the electrode material comprises graphite or other material sufficiently resistant to electrochemical corrosion by an aqueous based therapeutic agent solution. As an addition or alternative to reservoir 70, solution 80 and/or therapeutic agent 85 by itself may also be disposed in other locations within assembly 10. It may for example, be disposed within porous layer 50 (e.g., by injecting solution 80 into the porous layer prior to use, or the therapeutic agent can be coated onto the fibers of porous layer 50 with solution 80 subsequently added so that agent then dissolves in the solution). Still other embodiments, contemplate operably associating therapeutic agent solution 80 to assembly 10 by an external source, for example, an external reservoir (not shown) or other that is fluidically coupled to porous layer 50 or other portion of assembly 10.

In embodiments of electrode assembly 10 having a reservoir 70, the electrode assembly 10 can also include a self sealing port 12 fluidically coupled to reservoir 70 for filling the reservoir with therapeutic agent 80. The self sealing port 12 can comprise a silicone, or other elastomeric material, and allows the electrode assembly 10 to be filled with therapeutic solution 80 using a syringe and/or a mixing bottle with pointed tip and to do so using sterile technique. Typically, port 12 will include a channel 13 fluidically coupling the port 12 to the reservoir 70. In these and related embodiments, electrode 40 is sized and positioned within layer 20 such that a needle or other port penetrating tip used to do the injection, will not make contact with electrode 40. Also, an electrically insulating layer or barrier 14 can be positioned between port 12 and/or channel 13 and electrode 40 to minimize the likelihood of any electrical conduction between port 12 and/or channel 13 and the electrode. Barrier 14 can comprise various insulating polymers and other materials known in the art and can also have sufficient hardness to reduce the likelihood of penetration of electrode 40 by the needle tip or other port penetrating tip.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic electrode can be modified in material composition, size, and shape, depending upon one or more factors such as the type and amount of therapeutic agent; the tissue site, for the application of transdermal patch or other transdermal delivery device 5, and the projected wear time and conditions (e.g., hours vs. days, temperature, humidity, etc).

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A corrosion resistant electrode assembly for the iontophoretic transdermal delivery of a therapeutic agent, the assembly comprising:
   a conformable layer conformable to a contour of a skin surface, the conformable layer having a tissue contacting side and non-tissue contacting side;
   an electrical connector positioned on the non-tissue contacting side of the conformable layer, the connector configured to be coupled to an electrical power source;
   a tissue contacting porous layer positioned on the tissue contacting side of the conformable layer and operatively coupled to an electrode;
   wherein the electrode is operatively coupled to the connector and at least partially disposed in the porous layer, the electrode comprising an electrochemically un-reactive material such that the electrode does not substantially corrode when current flows through the electrode from the power source.

2. The electrode assembly of claim 1, wherein the electrode is in direct contact with the tissue contacting porous layer.

3. The electrode assembly of claim 2, wherein the electrode is positioned directly above the tissue contacting porous layer relative to the non-tissue contacting side of the conformable layer.

4. The electrode assembly of claim 1, wherein the electrode has a substantial disc shape.

5. The electrode assembly of claim 1, wherein the electrode has a thickness and flexibility allowing the electrode to bend and flex to conform to a contour of the skin surface while maintaining its anti-corrosion properties.

6. The electrode assembly of claim 1, wherein the electrode has radiused edges configured to minimize electrical edge effects.

7. The electrode assembly of claim 1, wherein the electrode material comprises graphite carbon.

8. The electrode assembly of claim 7, wherein the graphite carbon is solid graphite or compressed graphite.

9. The electrode assembly of claim 7, wherein the electrode has a thickness from about 0.5 mm to about 1 mm.

10. The electrode assembly of claim 1, wherein the electrode material comprises pyrolytic carbon.

11. The electrode assembly of claim 1, wherein the electrode material comprises carbon impregnated polymer.

12. The electrode assembly of claim 11, wherein the polymer is a rubber, polymer, polymer fiber, polyester fiber, or polysulphone fiber.

13. The electrode assembly of claim 1, wherein the electrode is configured such that an electrical impedance of the electrode does not substantially increase during periods of current flow through the electrode to the skin surface.

14. The electrode assembly of claim 13, wherein the periods of current flow are up to about 24 hours.

15. The electrode assembly of claim 13, wherein the periods of current flow are up to about 48 hours.

16. The electrode assembly of claim 13, wherein the periods of current flow are up to about 96 hours.

17. The electrode assembly of claim 1, wherein the electrode is sufficiently electrochemically un-reactive such that the electrode does not cause any substantial discoloration of the skin surface during a period of current flow through the electrode to the skin surface to deliver the therapeutic agent into the skin surface.

18. The electrode assembly of claim 1, wherein the electrode is sufficiently electrochemically un-reactive such that the electrode does not cause any irritation of the skin surface during a period of current flow through the electrode to the skin surface to deliver the therapeutic agent into the skin surface.

19. The electrode assembly of claim 1, wherein the electrode material comprises carbon or carbon impregnated fibers, the tissue contacting porous layer configured to substantially capture any carbon material dislodged from the electrode during periods of current flow through the electrode.

20. The electrode assembly of claim 19, wherein the tissue contacting porous layer comprises cotton.

21. The electrode assembly of claim 1, wherein the tissue contacting porous layer comprises foam or cotton.

22. The electrode assembly of claim 1, further comprising a reservoir for the therapeutic agent, wherein the reservoir is at least partially disposed in the tissue contacting layer and fluidically coupled to the tissue contacting porous layer.

23. The electrode assembly of claim 22, wherein the electrode is positioned directly above the reservoir relative to the non-tissue contacting side of the conformable layer.

24. The electrode assembly of claim 1, further comprising a therapeutic agent operatively associated with the electrode assembly.

25. The electrode assembly of claim 24, wherein the therapeutic agent comprises an ionic iron compound.

26. The electrode assembly of claim 24, wherein the therapeutic agent is disposed within the electrode assembly.

27. A system for the iontophoretic transdermal delivery of a therapeutic agent, the system comprising:
the electrode assembly of claim 1; and
an electrical power source operatively coupled to the electrode assembly.

* * * * *